US005843403A

United States Patent [19]
Dean

[11] Patent Number: 5,843,403
[45] Date of Patent: *Dec. 1, 1998

[54] RADIOLABLED GLUCANS COVALENTLY LINKED TO A RADIOMETAL BINDING MOIETY

[75] Inventor: Richard T. Dean, Bedford, N.H.

[73] Assignee: Diatide, Inc., Londonderry, N.H.

[ * ] Notice: The term of this patent shall not extend beyond the expiration date of Pat. No. 5,770,179.

[21] Appl. No.: 480,309

[22] Filed: Jun. 7, 1995

Related U.S. Application Data

[62] Division of Ser. No. 98,206, Jul. 28, 1993, abandoned.

[51] Int. Cl.$^6$ .......................... A61K 51/00; A61M 36/14
[52] U.S. Cl. ...................... 424/1.73; 424/1.11; 424/1.65; 534/14; 514/54; 536/123.12
[58] Field of Search .............................. 536/121, 123.12; 530/323, 331, 332, 345; 424/345, 1.11, 1.17, 1.21, 1.29, 1.73, 1.65, 1.37; 514/54, 62, 18; 534/10, 14

[56] References Cited

U.S. PATENT DOCUMENTS

| | | | |
|---|---|---|---|
| 4,385,046 | 5/1983 | Milbrath et al. | 424/1 |
| 4,431,626 | 2/1984 | Henze | 424/1.1 |
| 5,057,503 | 10/1991 | Czop et al. | 514/54 |
| 5,208,324 | 5/1993 | Klaveness et al. | 534/16 |
| 5,336,762 | 8/1994 | Ranney | 534/16 |
| 5,368,840 | 11/1994 | Unger | 424/9 |
| 5,422,095 | 6/1995 | Hasiguchi et al. | 424/1.73 |
| 5,443,815 | 8/1995 | Dean et al. | 424/1.41 |
| 5,561,220 | 10/1996 | Dean et al. | 424/1.69 |
| 5,582,172 | 12/1996 | Paposiv et al. | 128/683.4 |
| 5,607,677 | 3/1997 | Jamas et al. | 424/278.1 |

FOREIGN PATENT DOCUMENTS

| | | |
|---|---|---|
| WO9015596 | 12/1990 | WIPO . |
| WO9103248 | 3/1991 | WIPO . |
| WO9103495 | 3/1991 | WIPO . |
| WO9213572 | 8/1992 | WIPO . |
| WO9310747 | 6/1993 | WIPO . |
| WO9317719 | 9/1993 | WIPO . |
| WO9321962 | 11/1993 | WIPO . |
| WO9323085 | 11/1993 | WIPO . |
| WO9400489 | 1/1994 | WIPO . |
| WO9402068 | 2/1994 | WIPO . |

OTHER PUBLICATIONS

Di Luzio, "Macrophage Functional Status and Neoplasia," in *Pathophysiology of the Reticuloendothelial System*, (Altruo & Saba, eds.), Raven Press: NY, pp. 209–224.
Peters, 1992, "Imaging Inflammation: Current role of labled autologous leukocytes," *J. Nucl. Med.* 33: 65–67.
Onderdonk et al., 1992, "Anti–infective effect of poly–β1–3–glucopyranose glucan in vivo," *Infect. & Immun.* 60: 1642–1647.
Czop and Kay, 1991, "Isolation and Characterization of β–Glucan Receptors on Human Mononuclear Phagocytes," *J. Exp. Med.* 173: 1511–1520.

Lind et al., 1990, "Immunoscintigraphy of inflammatory processes with a technetium–99m–labled monoclonal anti–granulocyte antibody (MAb BW 250/183)," *J. Nucl. Med.* 31: 417–473.
Czop et al., 1989, "Phagocytosis of particulate activators of the human alternative complement pathway through monocyte β–glucan receptors," *Biochemistry of the Acute Allergic Reactions: Fifth International Symposium*, pp. 287–296.
Janusz et al., 1989, "Isolation of a yeast heptaglucoside that inhibits monocyte phagocytosis of zymosan particles," *J. Immunol.* 142: 959–965.
LaMuraglia et al., 1989, "Utility of the indium 111–labeled human immunoglobulin G scan for the detection of focal vascular graft infection," *J. Vasc. Surg.* 10: 20–28.
Vorne et al., 1989 "Technetium–99m HM–PAO–labled leukocytes in detection of inflammatory lesions: Comparison with gallium–67 citrate," *J. Nucl. Med*30: 1332–1336.
Czop, 1986, "The role of β–glucan receptors on blood and tissue leukocytes in phagocytosis and metabolic activation," *Pathol. Immunopathol.* 5: 286–296.
Czop and Austen, 1985, "A β–glucan inhibitable receptor on human monocytes: its identity with the phagocytic receptor for particulate activators of the alternative complement pathway," *J. Immunol.* 134: 2588–2593.
Ebright et al., 1992, "The gallium scan: Problems and misuse in examination of patients with suspected infection," *Arch. Int. Med.* 142: 246–254.
Bartnicki–Garcia, 1968, "Cell wall chemistry, morphogenesis and taxonomy of fungi," *Ann. Rev. Microbiol.* 22: 87–108.
Manners et al., 1974, "The Heterogeneity of Glucan Preparations from the Walls of Various Yeasts," *J. Gen. Microbiol.* 80: 411–417.
Her et al., 1987, "Simplified Approach to HPLC Precolumn Fluorescent Labeling of Carbohydrates: N–(2–Pyridinyl)–Glycosylamines," *J. Carbohydrate Chemistry* 6: 129–139.
Bogwald et al., 1986, "Coupling of Polysaccharides Activated by Means of Chloroacetaldehyde Dimethyl Acetal to Amines or Proteins by Reductive Amination," *Carbohydrate Research* 148: 101–107.
Smedsrod et al., "Fate of Intravenously Injected Animated Beta(1–3)Polyglucose Derivatized with 125I–Tyraminyl Cellobiose," *Immunopharmacology* 21(3): 149–158 (1991).
Rasmussen et al., "Dynamics of Blood Components and Peritoneal Fluid During Treatment of Murine E. Coli Sepsis With Beta–1, 3–Polyglucose Derivatives," *Scandinavian Journal of Immunology*, 32(4): 321–331 (1990).
Zubay, *Biochemistry*, 1983, pp. 438–446.

*Primary Examiner*—Gary E. Hollinden
*Assistant Examiner*—Dameron Jones
*Attorney, Agent, or Firm*—Patricia A. McDaniels; Kevin E. Noonan

[57] ABSTRACT

This invention relates to radiodiagnostic agents and reagents for preparing such agents, and also methods for producing radiolabeled radiodiagnostic agents. Specifically, the invention relates to technetium-99m ($^{99m}$Tc) labeled agents, methods and kits for making the agents, and methods for using the agents to image pathological sites, including sites of infection, inflammation, cancer and atherosclerosis in a mammalian body. Specifically the agents and reagents are derivatives of oligosaccharides, more specifically β-glucans.

7 Claims, No Drawings

RADIOLABLED GLUCANS COVALENTLY LINKED TO A RADIOMETAL BINDING MOIETY

This is a divisional of application Ser. No. 08/098,206, filed Jul. 28, 1993 now abandoned.

BACKGROUND OF THE INVENTION

1. Field of the Invention

This invention relates to radiodiagnostic agents and reagents for preparing such agents, and also methods for producing radiolabeled radiodiagnostic agents. Specifically, the invention relates to technetium-99m ($^{99m}Tc$) labeled agents, methods and kits for making the agents, and methods for using the agents to image pathological sites, including sites of infection, inflammation, cancer and atherosclerosis in a mammalian body. Specifically the agents and reagents are derivatives of oligosaccharides, more specifically β-glucans.

2. Description of the Prior Art

In the field of nuclear medicine, certain pathological conditions can be localized or the extent of such conditions determined by imaging the internal distribution of administered radioactively-labeled tracer compounds (i.e. radiotracers or radiopharmaceuticals) that accumulate specifically at the pathological site. This type of procedure is commonly known as radioimaging or scintigraphic imaging. Radioimaging has particular advantages over other methods of diagnosis in that it is essentially non-invasive, highly sensitive, highly specific, can be used to scan the entire body and is relatively cost-effective. A variety of radionuclides are known to be useful for radioimaging, including $^{67}Ga$, $^{68}Ga$, $^{99m}Tc$, $^{111}In$, $^{123}I$, $^{125}I$ or $^{201}Tl$.

There is a clinical need to be able to determine the location and/or extent of sites of focal or localized infection. In a substantial number of cases conventional methods of diagnosis (such as physical examination, x-ray, CT and ultrasonography) fail to identify such sites (e.g., an abscess). In some cases, biopsy may be resorted to, but is preferably avoided at least until it is necessary in order to identify the pathogen responsible for an abscess at a known location. Identifying the site of such "occult" infection is important because rapid localization of the problem is critical to effective therapeutic intervention.

An abscess may be caused by any one of many possible pathogens, so that a radiotracer specific for a particular pathogen would have limited scope. On the other hand, infection is almost invariably accompanied by inflammation, which is a general response of the body to tissue injury. Therefore, a radiotracer specific for sites of inflammation would be expected to be useful in localizing sites of infection caused by any pathogen.

One of the main phenomena associated with inflammation is the localization of leukocytes (white blood cells), including macrophages, monocytes and neutrophils, at the site of inflammation. A radiotracer specific for leukocytes would be useful in detecting leukocytes at the site of a localized infection.

Currently approved nuclear medicine procedures for imaging sites of infection use either indium-111 labeled leukocytes ($^{111}In$-WBC) (see, e.g. Peters, 1992, J. Nucl. Med. 33: 65–67) or gallium-67 ($^{67}Ga$) citrate (see, e.g. Ebright et al., 1982, Arch. Int. Med. 142: 246–254).

A major disadvantage of using $^{111}In$-labeled WBCs is that the preparation of the radiotracer requires sterile removal of autologous blood, sterile isolation of the leukocytes from the blood, sterile labeling of the leukocytes using conditions that do not damage the cells (since damaged WBC are taken up by the reticuloendothelial system when re-injected) and return (re-injection) of the (now labeled) leukocytes to the patient. Furthermore, a delay of 12 to 48 hours between injection and imaging may be required for optimal images. While $^{99m}Tc$ labeled leukocytes have been used to shorten this delay period (see, e.g. Vorne et al., 1989, J. Nucl. Med. 30: 1332–1336), ex-corporeal labeling is still required. A preferred radiotracer would be one that does not require removal and manipulation of autologous blood components.

$^{67}Ga$-citrate can be administered by intravenous injection. However, this compound is not specific for sites of infection or inflammation. Moreover, a delay of up to 72 hours is often required between injection of the radiotracer and imaging. In addition, the γ-(gamma) emission energies of $^{67}Ga$ are not well suited to conventional gamma cameras.

Radiolabeled monoclonal and polyclonal antibodies raised against human leukocytes (including monocytes, neutrophils, granulocytes and others) have been developed. $^{99m}Tc$ labeled antigranulocyte monoclonal antibodies (see, e.g. Lind et al., 1990, J. Nucl. Med. 31: 417–473) and $^{111}In$-labeled non-specific human immunoglobulin (see, e.g. LaMuraglia et al., 1989, J. Vasc. Surg. 10: 20–28) have been tested for the detection of inflammation secondary to infection. $^{111}In$-labeled IgG shares the disadvantages of $^{111}In$-labeled WBC, in that 24–48 hours are required between injection and optimal imaging. In addition, antibodies are difficult to produce and are associated with a safety concerns regarding potential contamination with biological pathogens (e.g. retroviruses).

In addition, the effective treatment of cancer by surgery or radiation therapy requires knowledge of the localization and extent of the disease. A means of monitoring the progression/regression of tumors following or during any form of therapy is also highly desirable. Advances in high-resolution imaging modalities such as CT and MRI allow the detection of many neoplasms. However certain tumors and their metastases are small and difficult to localize by these methods. Nuclear medicine offers a potentially more sensitive alternative. A radiotracer that selectively binds to or localizes to any and all cancerous tissue, sufficiently to allow easy external detection, might be considered to be the ultimate goal of radiodiagnostic oncology.

Also, despite remarkable advances in cardiology, coronary artery disease remains the leading cause of death in the U.S. The final event in this disease is usually fatal myocardial infarction caused by occlusive thrombosis of one or more coronary arteries usually at the site of a complicated atherosclerotic plaque. Therefore a means, preferably non-invasive, of determining the localization and/or extent of atherosclerotic plaque is highly desirable as an aid to selecting appropriate patient management. One of the most notable characteristics of atherosclerotic plaque is the accumulation of foam cells which are lipid-laden macrophages.

β-Glucans are oligoglucosides, which comprise 1,3 and 1,6 linked β-D-glucose residues, originally discovered as components of yeast and fungal cell walls (Bartnicki-Garcia in Ann Rev Microbiol. 1968, 22, 87). Originally obtained in an insoluble form, β-glucans have since been obtained as soluble, low molecular weight oligomers (Janusz, Austen and Czop, J. Immunol. (1989), 142, (959–965). They have been shown to be active in enhancing the host defense mechanisms of mammals by activating the alternative complement pathway through their specific binding to receptors (called β-glucan receptors) found on the cell-surfaces of monocytes, macrophages and neutrophils (Czop and Kay, J. Exp. Med. (1991), 173, 1511–1520, Czop et al, Biochemistry of the Acute Allergic Reactions: Fifth International Symposium. (1989), 287–296 and J. K. Czop, Pathol. Immunopathol. Res (1986), 5, 286–296, Czop and Austen, J. Immunol. (1985), 134, 2588–2593). The in vivo administration of particulate β-glucans has been shown to provide protection from many pathogens including bacteria, viruses and fungi as well as reducing tumor growth (Czop et al, Biochemistry of the Acute Allergic Reactions: Fifth International Symposium. 1989, 287–296). The smallest active β-glucan reported so far is a heptaglucoside (Janusz et al, J Immunol 1989,142,959. Onderdonk and co-workers (Infection and Immunity, 1992, 60, 1642–1647) describe the antiinfective properties of this small β-glucan. The β-glucans have also been shown to exhibit an anti-tumor growth effect, believed to occur by increasing the number of macrophages localizing to tumors (Di Luzio in Pathophysiology of the Reticuloendothelial System (Eds Altruo and Saba), Raven Press, NY, pp209–224).

Czop and Janusz, U.S. Pat,. No. 5,057,503 (1991), claim a heptaglucoside capable of reacting with β-glucan receptors, their isolation and their therapeutic use.

Jamas et al, PCT/US90/03440 claim β-glucans as drug delivery vehicles and as adjuvants.

Jamas et al, PCT/US90/05022 claim a method of activating the immune system by administering β-glucans.

Jamas et al, PCT/US90/05041 claim a method of producing a soluble β-glucan.

Methods for preparing radiolabel-binding moieties and of labeling them with $^{99m}$Tc are disclosed in co-pending U.S. patent applications Ser. Nos. now abandoned, which issued as U.S. Pat. No. 5,654,272; 07/757,470, now U.S. Pat. No. 5,225,180; 07/807,062, now U.S. Pat. No. 5,443,815; 07/851,074, now abandoned, which issued as U.S. Pat. No. 5,711,931; 07/871,282, a divisional of which issued as U.S. Pat. No. 5,720,934; 07/886,752, now abandoned, a continuation of which has been allowed as U.S. Ser. No. 08/273,274; 07/893,981, now U.S. Pat. No. 5,508,020; 07/955,466; 07/977,628, now U.S. Pat. No. 5,405,597; 08/019,525, now U.S. Pat. No. 5,552,525; 08/044,825, now abandoned, which issued as U.S. Pat. No. 5,645,815; and 08/073,577, now U.S. Pat. No. 5,561,220; and PCT International Applications PCT/US92/00757, PCT/US92/10716, PCT/US93/02320, PCT/US93/03687, PCT/US93/04794, and PCT/US93/06029, which are hereby incorporated by reference.

SUMMARY OF THE INVENTION

The present invention provides scintigraphic imaging agents that are β-glucans which are radiolabeled with a radioisotope or are β-glucan-derived reagents radioactively-labeled with a radioisotope. The β-glucan-derived reagents of the invention are comprised of a β-glucan covalently linked to a radiolabel binding moiety. The scintigraphic imaging agents of this invention are useful for imaging pathological sites within a mammalian body including sites of infection, inflammation, cancer and atherosclerosis.

A first aspect of the invention comprises reagents for preparing scintigraphic imaging agents for imaging sites within a mammalian body, said reagents comprising a β-glucan having a 1,3 and 1,6 linked D-glucoside sequence, of molecular weight of up to about 2,000 kDa and a radiolabel-binding moiety.

In a second aspect, the scintigraphic imaging agent of the invention comprises a soluble β-glucan.

In a third aspect, the scintigraphic imaging agent of the invention comprises the radioisotope $^{99m}$Tc.

In another aspect of the invention the radiolabel-binding moiety is linked to the β-glucan via a 1-amino or 1-thio substituent.

In yet another aspect, the reagents of the invention comprise a β-glucan and a radiolabel-binding moiety of formula

Cp(aa)Cp     (I)

wherein Cp is a protected cysteine residue and (aa) stands for an amino acid, and wherein the radiolabel-binding moiety is covalently linked to the β-glucan. In a preferred embodiment, the amino acid is glycine. In another preferred embodiment, the radiolabel-binding moiety is linked to the β-glucan via a linker which forms either an ether, thioether or amine bond to the β-glucan.

In another aspect, the invention provides reagents comprising a radiolabel-binding moiety having the following structure:

A—CZ(B)—[C(R$^1$R$^2$)]$_n$—X     II.

wherein A is H, HOOC, H$_2$NOC, (β-glucan)-(linker)-NHOC, (β-glucan)-(linker)-OOC or R$^4$; B is H, SH or —NHR$^3$, —N(R$^3$)-(linker)-(β-glucan) or R$^4$; X is SH or —NHR$^3$, —N(R$^3$)-(linker)-(β-glucan) or R$^4$; R$^1$, R$^2$, R$^3$ and R$^4$ are independently H or straight or branched chain or cyclic lower alkyl; n is 0, 1 or 2; and: (1) where B is —NHR$^3$ or —N(R$^3$)-(linker)-(β-glucan), X is SH and n is 1 or 2; (2) where X is —NHR$^3$ or —N(R$^3$)-(linker)-(β-glucan), B is SH and n is 1 or 2; (3) where B is H or R$^4$, A is HOOC, H$_2$NOC, (β-glucan)-(linker)-NHOC or (β-glucan)-(linker)-OOC, X is SH and n is 0 or 1; (4) where A is H or R$^4$, then where B is SH, X is —NHR$^3$ or —N(R$^3$)-(linker)-(β-glucan) and where X is SH, B is —NHR$^3$ or —N(R$^3$)-(linker)-(β-glucan); (5) where X is H or R$^4$, A is HOOC, H$_2$NOC, (β-glucan)-(linker)-NHOC or (β-glucan)-(linker)-OOC and B is SH; (6) where Z is methyl, X is methyl, A is HOOC, H$_2$NOC, (β-glucan)-(linker)-NHOC or (β-glucan)-(linker)-OOC and B is SH and n is 0; and wherein the thiol moiety is in the reduced form.

In yet another aspect, the present invention provides reagents comprising β-glucans covalently linked to a radiolabel-binding moiety having the following structure:

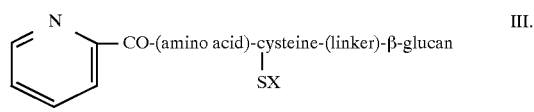

III.

For purposes of this invention, radiolabel-binding moieties having structure III will be referred to as picolinic acid (Pic)-based moieties; or

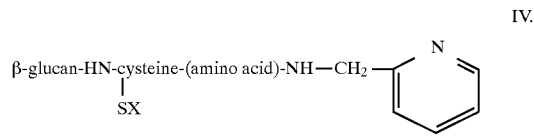

IV.

For purposes of this invention, radiolabel-binding moieties having structure IV will be referred to as picolylamine (Pica)-based moieties; wherein X is H or a protecting group; (amino acid) is any amino acid. In a preferred embodiment, the amino acid is glycine and X is an acetamidomethyl protecting group.

In yet another embodiment of the invention, reagents are provided for preparing scintigraphic imaging agents for imaging sites within a mammalian body, comprising a β-glucan and a bisamino bisthiol radiolabel-binding moiety covalently linked to the β-glucan. The bisamino bisthiol radiolabel-binding moiety in this embodiment of the invention has a formula selected from the group consisting of:

V.

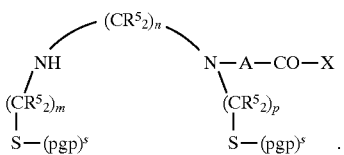

wherein each $R^5$ can be independently H, $CH_3$ or $C_2H_5$; each $(pgp)^s$ can be independently a thiol protecting group or H; m, n and p are independently 2 or 3; A is linear or cyclic lower alkyl, aryl, heterocyclyl, combinations or substituted derivatives thereof; and X is (linker)-β-glucan;

VI.

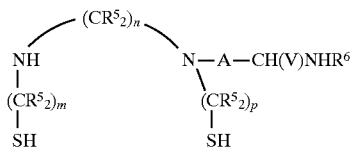

wherein each $R^5$ is independently H, lower alkyl having 1 to 6 carbon atoms, phenyl, or phenyl substituted with lower alkyl or lower alkoxy; m, n and p are independently 1 or 2; A is linear or cyclic lower alkyl, aryl, heterocyclyl, combinations or substituted derivatives thereof; V is H or —CO-(linker)-β-glucan; $R^6$ is H or a (linker)-β-glucan; provided that when V is H, $R^6$ is a (linker)-β-glucan and when $R^6$ is H, V is a —CO-(linker)-β-glucan. For purposes of this invention, radiolabel-binding moieties having these structures will be referred to as "BAT" moieties.

The invention comprises scintigraphic imaging agents that are complexes between β-glucans or the reagents of the invention and $^{99m}$Tc, and methods for radiolabeling the β-glucans and reagents of the invention with $^{99m}$Tc. Radiolabeled complexes provided by the invention may be formed by reacting β-glucans or the reagents of the invention with $^{99m}$Tc in the presence of a reducing agent. Preferred reducing agents include but are not limited to dithionite ion, stannous ion and ferrous ion. Complexes of the invention are also formed by labeling β-glucans or the reagents of the invention with $^{99m}$Tc by ligand exchange of a prereduced $^{99m}$Tc complex as provided herein.

The invention also provides kits for preparing scintigraphic imaging agents that are β-glucans or the reagents of the invention radiolabeled with $^{99m}$Tc. Kits for labeling the β-glucans or the reagents provided by the invention with $^{99m}$Tc are comprised of a sealed vial containing a predetermined quantity of a β-glucan or a reagent of the invention and a sufficient amount of reducing agent to label the β-glucan or reagent with $^{99m}$Tc.

This invention provides methods for using scintigraphic imaging agents that are radiolabeled β-glucans and reagents for imaging pathological sites, including infection, inflammation, cancer and atherosclerosis within a mammalian body by obtaining in vivo gamma scintigraphic images. These methods comprise administering an effective diagnostic amount of radiolabeled β-glucan or reagent of the invention and detecting the gamma radiation emitted by the radiolabel localized at the pathological site within the mammalian body.

Specific preferred embodiments of the present invention will become evident from the following more detailed description of certain preferred embodiments and the claims.

DETAILED DESCRIPTION OF THE INVENTION

The β-glucans of this invention have linear or branched 1,3 and 1,6 linked D-glucoside sequences. They comprise both insoluble and soluble molecular entities having molecular weights of up to about 2,000 kDa. In a preferred embodiment, the β-glucan is soluble. Most preferably the soluble β-glucan is a poly-β1-6-glucotriosyl-β1-3-glucopyranose.

In Cp(aa)Cp-containing β-glucan reagents, the Cp is a protected cysteine where the S-protecting groups are the same or different and may be but are not limited to:
- —$CH_2$-aryl (aryl is phenyl or alkyl or alkyloxy substituted phenyl);
- —CH-(aryl)$_2$, (aryl is phenyl or alkyl or alkyloxy substituted phenyl);
- —C-(aryl)$_3$, (aryl is phenyl or alkyl or alkyloxy substituted phenyl);
- —$CH_2$-(4-methoxyphenyl);
- —CH-(4-pyridyl)(phenyl)$_2$;
- —C($CH_3$)$_3$
- -9-phenylfluorenyl;
- —$CH_2$NHCOR (R is unsubstituted or substituted alkyl or aryl);
- —$CH_2$—NHCOOR (R is unsubstituted or substituted alkyl or aryl);
- —CONHR (R is unsubstituted or substituted alkyl or aryl);
- —$CH_2$—S—$CH_2$-phenyl The preferred protecting group has the formula —$CH_2$—NHCOR wherein R is a lower alkyl having 1 and 8 carbon atoms, phenyl or phenyl-substituted with lower alkyl, hydroxyl, lower alkoxy, carboxy, or lower alkoxycarbonyl.

β-Glucans of the present invention can be obtained from natural sources, such as yeast, by methods well known in the art (e.g. see Manners, Masson and Patterson in J. Gen. Microbiol. (1974), 80, 411–417). Small soluble β-glucans can be obtained from larger β-glucans by methods known in the art (e.g. as described by Janusz, Austen and Czop in J. Immunol. (1989),142, 959–965 and Jamas et al, PCT/US90/05041) or can be obtained by chemical synthesis. Preferred soluble β-glucans are poly-β11 -6-glucotriosyl-β1-3-glucopyranoses including those that are heptaglucosides. The term soluble β-glucan is used herein to mean soluble in a physiologically compatible solution to about 10 mg/mL.

The reagents of this invention comprise a β-glucan covalently attached to a radiolabel-binding moiety. The radiolabel binding moiety can be attached directly to the β-glucan or it can be attached via a linker. The direct attachment of the radiolabel-binding moiety may be advantageously made by a 1-thioether or 1-amino group, or via an ester or ether bond to any hydroxyl group of the β-glucan (see for example, Her, Santikarn and Reinhold, J. Carbohydrate Chemistry (1987), 6, 129–139 and Bogwald, Seljelid and Hoffman, Carbohydrate research (1986), 148, 101–107). The linker is normally a small entity, of less than about 500 Da formula weight and may advantageously be a small (up to about 10 carbon atoms) linear or branched chain divalent alkyl, alkaryl or aryl group, optionally comprising a multiplicity of hetero atoms, preferably oxygens, and optionally substituted, preferably with hydrophilic moieties.

In forming a complex of radioactive technetium with the β-glucans and the reagents of this invention, the technetium complex, preferably a salt of $^{99m}$Tc pertechnetate, is reacted with the β-glucan or reagent in the presence of a reducing agent. Preferred reducing agents are dithionite, stannous and ferrous ions; the most preferred reducing agent is stannous chloride. Means for preparing such complexes are conveniently provided in a kit form comprising a sealed vial containing a predetermined quantity of a β-glucan or reagent of the invention to be labeled and a sufficient amount of reducing agent to label the reagent with $^{99m}$Tc. Alternatively, the complex may be formed by reacting a β-glucan or reagent of this invention with a pre-formed labile complex of technetium and another compound known as a transfer ligand. This process is known as ligand exchange and is well known to those skilled in the art. The labile complex may be formed using such transfer ligands as tartrate, citrate, gluconate or mannitol, for example. Among the $^{99m}$Tc pertechnetate salts useful with the present invention are included the alkali metal salts such as the sodium salt, or ammonium salts or lower alkyl ammonium salts.

The reaction of β-glucans and reagents of this invention with $^{99m}$Tc-pertechnetate or preformed $^{99m}$Tc labile complex can be carried out in an aqueous medium at room temperature or with heating for a short period (from 5 to about 60 minutes). When an anionic complex having a charge of [−1] is formed in the aqueous medium in the form of a salt with a suitable cation such as sodium cation, ammonium cation, mono, di- or tri-lower alkyl amine cation, etc. Any conventional salt of the anionic complex with a pharmaceutically acceptable cation can be used in accordance with this invention.

In a preferred embodiment of the invention, a kit for preparing $^{99m}$Tc-labeled β-glucans and β-glucan reagents is provided. An appropriate amount of the β-glucan or reagent is introduced into a vial containing a reducing agent, such as stannous chloride, in an amount sufficient to label the β-glucan or reagent with $^{99m}$Tc. An appropriate amount of a transfer ligand as described (such as tartrate, citrate, gluconate or mannitol, for example) can also be included. In forming the $^{99m}$Tc complexes, it is generally preferred to form radioactive complexes in solutions containing radioactivity at concentrations of from about 0.01 millicurie (mCi) to 100 mCi per ml.

Scintigraphic imaging agents of this invention can also be prepared by incubating radiolabeled β-glucans or radiolabeled β-glucan reagents with leukocytes, wherein the leukocytes take up the radiolabeled species and can then be administered as radiolabeled leukocytes.

The radiolabeled scintigraphic imaging agents provided by the present invention can be used for visualizing pathological sites including sites of inflammation and infection, including abscesses and sites of "occult" infection and inflammatory bowel disease. The imaging agents provided can also be used to image sites of atherosclerotic plaque and also tumors. In accordance with this invention, the scintigraphic imaging agents are administered in a single unit injectable dose. Any of the common carriers known to those with skill in the art, such as sterile saline solution or plasma, can be utilized after radiolabeling for preparing the injectable solution to diagnostically image various organs, tumors and the like in accordance with this invention. Generally, the unit dose to be administered has a radioactivity of about 0.01 mCi to about 100 mCi, preferably 1 mCi to 20 mCi. The solution to be injected at unit dosage is from about 0.01 ml to about 10 ml. After intravenous administration, imaging of the organ or tumor in vivo can take place in a matter of a few minutes. However, imaging can take place, if desired, in hours or even longer, after injecting into patients. In most instances, a sufficient amount of the administered dose will accumulate in the area to be imaged within about 0.1 of an hour to permit the taking of scintiphotos. Any conventional method of scintigraphic imaging for diagnostic purposes can be utilized in accordance with this invention.

The scintigraphic imaging agents provided by the invention may be administered intravenously in any conventional medium for intravenous injection such as an aqueous saline medium, or in blood plasma medium. Such medium may also contain conventional pharmaceutical adjunct materials such as, for example, pharmaceutically acceptable salts to adjust the osmotic pressure, buffers, preservatives and the like. Among the preferred media are normal saline and plasma.

The methods for making and labeling these compounds are more fully illustrated in the following Examples. These Examples illustrate certain aspects of the above-described method and advantageous results. These Examples are shown by way of illustration and not by way of limitation.

EXAMPLE 1

Reagent Synthesis

DMSO=dimethyl sulfoxide, DMF=N,N-dimethylformamide and DIEA=N,N-diisopropylethylamine.

Poly-β1-6-glucotriosyl-β1-3-glucopyranose (PGG) is obtained using the procedures described by Jamas et al (PCT/US90/05041).

N-α-Boc-lysyl-glycyl-(S-trityl)cysteine amide, glycyl-glycyl-(S-trityl)cysteine amide and chloroacetyl-(S,S'-bis-acetamidomethyl)cysteinyl-glycyl-cysteine amide are prepared by solid phase or solution phase peptide synthesis and are purified by reverse phase HPLC.

A conjugate with $N^1,N^4$-bis(2-mercapto-2-methylpropyl)-1,4,10-triazadecane is obtained by reacting a β-glucan (e.g., PGG) at from about 1 to 100mg/mL with about 1.5 mmol $N^1$-(t-butoxycarbonyl)-$N^1,N^4$-bis(2-methyl-2-triphenylmethylthiopropyl)-1,4,10-triazadecane in water, Cellosolve or mixtures thereof at approximately pH 7 at about 65° C. for from 1 to about 10 hours, followed by reduction with NaBH$_3$CN followed by deprotection with trifluoroacetic acid. The product is purified by preparative HPLC.

Similarly conjugates of ε-(lysyl-glycyl-cysteine amide) and glycyl-glycyl-cysteine amide are prepared from N-α-Boc-lysyl-glycyl-(S-trityl)cysteine amide and glycyl-glycyl-(S-trityl)cysteine amide respectively.

A conjugate of $N^6,N^9$-bis(2-mercapto-2-methylpropyl)-6,9-diazanonanoic acid is prepared by reacting β-glucan (e.g. PGG) at from about 1 to 100 mg/mL in water, DMSO or DMF containing about 1.5 mmol DIEA and optionally containing about 0.15 mmol 4-dimethylaminopyridine, with about 1.5 mmol of the N-hydroxysuccinimide ester of $N^9$-(t-butoxycarbonyl)-$N^6,N^9$-bis(2-methyl-2-triphenylmethylthiopropyl)-6,9-diazanonanoic acid, at room temperature, followed by deprotection with TFA and purification by HPLC.

A conjugate of (S,S'-bis-acetamidomethyl)cysteinyl-glycyl-cysteine amide is prepared by reacting β-glucan (e.g. PGG) at from about 1 to 100 mg/mL in DMSO, with sodium methylsulfinylmethanide, or another suitable base, (approx. 1.6 mmol base/100 mg β-glucan) for from 1 to about 24 hours and reacting the resultant mixture with approx. 1.6 mmol chloroacetyl-(S,S'-bis-acetamidomethyl)cysteinylglycyl-cysteine amide for about 1 to 5 hours at between 20° and 50° C., followed by purification by HPLC.

EXAMPLE 2

A General Method for Radiolabeling with Tc-99m

1. About 0.1 mg of a β-glucan or a reagent prepared as in Example 1 is dissolved in 0.1 mL of water or 50/50 ethanol/water. Approximately 100 μg stannous salt as stannous chloride pre-dissolved in methanol, or stannous tartrate pre-dissolved in water is added followed by 1–10 mCi $^{99m}$Tc pertechnetate in approximately 0.1 mL. The mixture is allowed to stand for 15–30 minutes at room temperature or at 100° C. For soluble β-glucans the preparation is then filtered through a 0.2 μm filter and the Tc-99m labeled product purity is determined by HPLC. The purity of insoluble β-glucan products is assessed by ITLC developed in saline.

2. About 0.1 mg of β-glucan or reagent prepared as described in Example 1 is dissolved in 0.1 mL of water or 50/50 ethanol/water or phosphate-buffered saline or 50 mM potassium phosphate buffer (pH=5, 6 or 7.4). Tc-99m gluceptate was prepared by reconstituting a Glucoscan vial (E.I. DuPont de Nemours, Inc.) with 1.0 mL of Tc-99m sodium pertechnetate containing up to 200 mCi and allowed to stand for 15 minutes at room temperature. 25 μl of Tc-99m gluceptate was then added to the peptide and the reaction allowed to proceed at room temperature or at 100° C. for 15–30 min. For soluble β-glucans the preparation is then filtered through a 0.2 μm filter and the Tc-99m labeled product purity is determined by HPLC. The purity of insoluble β-glucan products is assessed by ITLC developed in saline.

What is claimed is:

1. A reagent for preparing a scintigraphic imaging agent comprising a specific binding β-glucan covalently linked to a radiometal-binding moiety, wherein the β-glucan is linked to the moiety by a linkage selected from the group consisting of a direct covalent linkage and a linker having a molecular weight less than about 500 Da.

2. The reagent of claim 1, wherein the β-glucan is soluble in a physiologically compatible solution to about 10 mg/ml.

3. A reagent for preparing a scintigraphic imaging agent comprising a poly-β1-6-glucotriosyl-β1-3-glucopyranose covalently linked to a radiometal-binding moiety.

4. A reagent for preparing a scintigraphic imaging agent comprising a specific binding β-glucan covalently linked to a radiometal-binding moiety having a formula selected from the group consisting of:

(a) C(pgp)$^S$-(aa)-C(pgp)$^S$
wherein (pgp)$^S$ is H or a thiol protecting group and (aa) is an amino acid;

(b) a radiometal complexing group comprising a single thiol moiety having a formula:

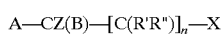

wherein

A is H, HOOC, H$_2$NOC, (β-glucan)-(linker)-NHOC, (β-glucan)-(linker)-OOC or R'''';

B is H, SH, —NHR''', —N(R''')-(linker)-(β-glucan), or R'''';

X is H, SH, —NHR''', —N(R''')-(linker)-(β-glucan) or R'''';

Z is H or R'''';

R', R'', R''' and R'''' are independently H or lower straight or branched chain or cyclic alkyl;

n is 0, 1 or 2;

and where B is —NHR''' or —N(R''')-(linker)-(β-glucan), X is SH, and n is 1 or 2;

where X is —NHR''' or —N(R''')-(linker)-(β-glucan), B is SH, and n is 1 or 2;

where B is H or R'''', A is HOOC, H$_2$NOC, (β-glucan)-(linker)-NHOC, (β-glucan)-(linker)-OOC, X is SH, and n is 0 or 1;

where A is H or R'''', then where B is SH, X is —NHR''' or —N(R''')-(linker)-(β-glucan) and where X is SH, B is —NHR''' or —N(R''')-(linker)-(β-glucan);

where X is H or R'''', A is HOOC, H$_2$NOC, (β-glucan)-(linker)-NHOC, (β-glucan)-(linker)-OOC and B is SH;

where Z is methyl, X is methyl, A is HOOC, H$_2$NOC, (β-glucan)-(linker)-NHOC, (β-glucan)-(linker)-OOC, B is SH and n is 0;

and wherein (β-glucan) represents the covalent attachment of the radiometal binding moiety to the specific binding β-glucan;

(c)

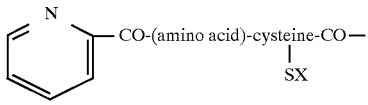

wherein

X=H or a protecting group;

(amino acid)=any amino acid;

(d)

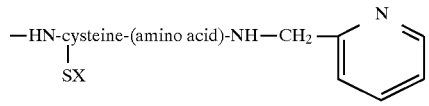

wherein

X=H or a protecting group;

(amino acid)=any amino acid;

(e)

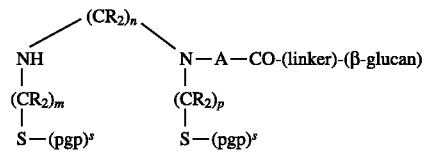

wherein each R is independently H, CH$_3$ or C$_2$H$_5$;

each (pgp)$^S$ is independently a thiol protecting group or H;

m, n and p are independently 2 or 3;

A=linear or cyclic lower alkyl, aryl, heterocyclyl, a combination thereof, or a substituted derivative thereof;

and (f)

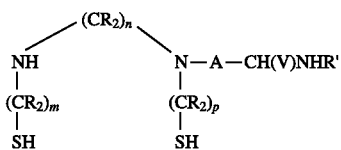

wherein each R is independently H, CH$_3$ or C$_2$H$_5$;

m, n and p are independently 2 or 3;

A=linear or cyclic lower alkyl, aryl, heterocyclyl, a combination thereof or a substituted derivative thereof;

V=H or —CO-(linker)-(β-glucan);

R'=H or (linker)-(β-glucan);

and wherein when V=H, R'=-(linker)-(β-glucan) and when R'=H, V=—CO-(linker)-(β-glucan);

wherein (linker) is a bond or a divalent radical covalently attached to the β-glucan and to the radiometal-binding moiety and wherein β-glucan represents the covalent attachment of the radiometal binding moiety to the β-glucan.

5. The reagent of claim 4 wherein the radiometal-binding moiety is

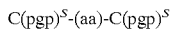

and wherein (pgp)$^S$ has a formula

wherein R is a lower alkyl having 1 to 6 carbon atoms, 2-pyridyl, 3-pyridyl, 4-pyridyl, phenyl, or phenyl substituted with lower alkyl, hydroxy, lower alkoxy, carboxy, or lower alkoxycarbonyl.

6. The reagent of claim 4 wherein the radiometal-binding moiety has a formula:

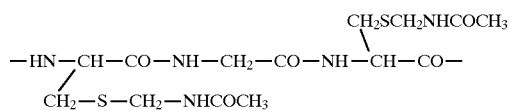

7. The reagent of claim 1, wherein the β-glucan comprises a multiplicity of 1,3- and 1,6-linked D-glucoside residues.

* * * * *